(12) United States Patent
Sarpeshkar et al.

(10) Patent No.: US 8,700,166 B2
(45) Date of Patent: Apr. 15, 2014

(54) CODING FOR VISUAL PROSTHESES

(75) Inventors: Rahul Sarpeshkar, Arlington, MA (US); Lorenzo Turicchia, Cambridge, MA (US); Soumyajit Mandal, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 908 days.

(21) Appl. No.: 12/537,444

(22) Filed: Aug. 7, 2009

(65) Prior Publication Data

US 2010/0036457 A1 Feb. 11, 2010

Related U.S. Application Data

(60) Provisional application No. 61/086,898, filed on Aug. 7, 2008.

(51) Int. Cl.
*A61B 1/00* (2006.01)

(52) U.S. Cl.
USPC ............................................................ 607/53

(58) Field of Classification Search
USPC ............................................................ 607/53
See application file for complete search history.

(56) References Cited

U.S. PATENT DOCUMENTS

| | | | |
|---|---|---|---|
| 6,400,989 B1 * | 6/2002 | Eckmiller | 607/54 |
| 6,920,358 B2 | 7/2005 | Greenberg et al. | |
| 7,075,993 B2 | 7/2006 | O'Brien | |
| 7,356,185 B2 | 4/2008 | Gewaltig et al. | |
| 2003/0181957 A1 * | 9/2003 | Greenberg et al. | 607/54 |
| 2006/0106432 A1 | 5/2006 | Sawan et al. | |
| 2007/0060984 A1 | 3/2007 | Webb et al. | |

OTHER PUBLICATIONS

*PCT International Search Report*, PCT/US09/53102 mailed Sep. 15, 2009 (3 pages).
Wilson, Blake S., et al. "Better speech recognition with cochlear implants" *Letters to Nature*, vol. 352 (Jul. 18, 1991) pp. 236-238.
Cha, Kichul, et al. "Mobility Performance with a Pixelized Vision System" *Vision Res.* vol. 32, No. 7 (1992) pp. 1367-1372.
Dowling, Jason A., et al. "Mobility Enhancement and Assessment for a Visual Prosthesis" School of Electrical and Electronic Systems Engineering—Queensland University of Technology, Brisbane, Australia (2004) 13 pages.
Pezaris, John S., et al. "Demonstration of artificial visual percepts generated through thalamic microstimulation" *Proceedings of the National Academy of Sciences of the United States of America*, vol. 104, No. 18 (Apr./May 2007) pp. 7670-7675.
Wilson, Blake S., et al. "Design and evaluation of a continuous interleaved sampling (CIS) processing strategy for multichannel cochlear implants" *Journal of Rehabilitation Research and Development*, vol. 30, No. 1 (1993) pp. 110-116.

(Continued)

*Primary Examiner* — George Manuel
(74) *Attorney, Agent, or Firm* — Occhiuti & Rohlicek LLP

(57) ABSTRACT

A visual prostheses codes visual signals into electrical stimulation patterns for the creation of artificial vision. In some examples, coding of the information uses image compression techniques, temporal coding strategies, continuous interleaved sampling (CIS), and/or radar or sonar data. Examples of the approach are not limited to processing visual signals but can also be used to processing signals at other frequency ranges (e.g., infrared, radio frequency, and ultrasound), for instance, creating an augmented visual sensation.

29 Claims, 4 Drawing Sheets

(56) References Cited

OTHER PUBLICATIONS

Sit, Ji-Jon, et al. "A Low-Power Asynchronous Interleaved Sampling Algorithm for Cochlear Implants That Encodes Envelope and Phase Information" *IEEE Transactions on Biomedical Engineering*, vol. 54, No. 1 (Jan. 2007) pp. 138-149.

Sarpeshkar, Rahul, et al. "Low-Power Circuits for Brain-Machine Interfaces" *IEEE Transactions on Biomedical Circuits and Systems*, vol. 2, No. 3 (Sep. 2008) pp. 173-183.

Turicchia, L., et al. "A Low-Power Imager and Compression Algorithms for a Brain-Machine Visual Prosthesis for the Blind" (Aug. 29, 2008) 13 pages.

* cited by examiner

CODING FOR VISUAL PROSTHESES

CROSS-REFERENCE TO RELATED APPLICATIONS

This application claims the benefit of U.S. Provisional Application No. 61/086,898 filed Aug. 7, 2008, the contents of which are incorporated herein by reference.

BACKGROUND

This document relates to coding for visual prostheses.

According to the World Health Organization, in 2002 more than 161 million people were visually impaired, of whom 124 million had low vision and 37 million were blind. Moreover, blindness has been estimated to cost the US federal government alone $4 billion a year. An artificial vision system is expected to have a huge impact on society and preliminary results with visual prosthesis devices now under development are very encouraging.

Neural tissue can be stimulated by pulses of electrical current through electrodes. Visual sensation can be created by stimulating neural tissues used during visual processing. Currently, the four main approaches to visual prosthesis involve cortical implants, retinal implants, optic nerve cuff electrodes, and dorsal lateral geniculate nucleus (LGN) implants. The last approach has been proposed recently, and preliminary results suggest that this approach has great promise. In this kind of implant, electrodes directly stimulate the LGN, which is the part of the thalamus that relays signals from the retina to the primary visual cortex (also known as V1).

The visual information, which may be obtained using a camera, can be coded in electrical pulses, which are relayed to the nervous system via the electrodes of the prosthetic device. It has been shown that an image with a 25×25 array of pixels allows suitable face recognition, mobility, and reading speed. However, only a much smaller number of electrodes is currently available in state-of-the-art prostheses.

SUMMARY

In one aspect, in general, a method for coding information for prosthetic visual presentation includes sequentially selecting portions of an image. For each selected portion, a set of values are formed to represent the portion, and signals are formed for presentation of the set of values representing the portion of the image on corresponding electrodes. This includes forming signals for sequential presentation of multiple disjoint subsets of the values in corresponding successive time intervals.

Aspects may include one or more of the following features.

The sequential selection of portions of the image, and forming the values and forming the signals for the selected portions, are repeated for successive images.

Forming the set of values to represent the selected portion of the image includes forming subunits of the portion, and forming a subset of the values to represent each subunit.

Each of the disjoint subsets of values includes values used to represent multiple of the subunits of the selected portion.

The image is represented as a set of scan lines of pixels, and each selected portion includes a corresponding subset of the scan lines of the image. For instance, each portion forms a column or a row of the image.

Forming the set of values to represent the selected portion of the image includes forming blocks of pixels in the subset of scan lines, and forming a transform representation of each of the blocks of pixels.

Forming the transform representation includes forming values as Discrete Cosine Transform (DCT) coefficients of the block of pixels. Forming the values as DCT coefficients may includes disregarding at least some DCT coefficients of the block of pixels.

Each disjoint subset of values includes corresponding values of a particular DCT coefficient of multiple of the blocks of pixels.

Sequentially selecting the portions of the image includes sequentially selecting the portions in a predetermined cycle.

Sequentially selecting the portions of the image includes selecting portions of the image according to a control signal. The control signal may represent at least one of a joystick signal and an eye tracking signal.

Sequentially selecting portions of the image includes selecting processing of the image according to selected kernel functions. The kernel functions may include a set of Gabor kernel functions, each characterized by at least a frequency, rotation, and/or scale parameter.

Forming the values representing the selected portion of the image includes forming quantized values.

The formed signals are presented to a subject to elicit a perception of the image. For instance, electrodes are driven using the formed signals. The formed signals can be, for instance, voltage encoded or current encoded electrical signals, optical signals, or radio-frequency signals.

For each selected portion of the image, driving the electrodes includes driving a different subset of electrodes using each different disjoint subset of the values.

Driving the electrodes includes transmitting the formed signal to a region of one or more of a retina, an optic nerve, a thalamus, and a cortex of a brain.

The image is acquired from an imager that includes one or more of a video camera, a still-frame camera, a radar sensor, a sonar sensor, and an ultrasonic sensor. The imager may be controlled using an external signal. For instance, the external signal is provided by one or more of an eye-tracking system, physiological measurements, a joystick, or a keyboard.

The image can be an image of one or more of a landscape, a face, or text.

A graphical element is added to the image that is indicative of a part of the image that is currently selected.

The image includes a graphical representation of text, each portion of the image including at least one character of the text.

The graphical representation of the text includes at least one of a graphical representation of a character glyph, a Braille code, a Morse code, and a user-defined code.

In another aspect, in general, a visual prosthesis includes an input for accepting a signal representing an input image, a signal processor, and an output. The signal processor is configured to sequentially select portions of the image, and for each selected portion, form values to represent the portion, and form signals for presentation of the values representing the portion of the image on corresponding electrodes, including forming signals for sequential presentation of multiple disjoint subsets of the values in successive time intervals. The output is used to provide the formed signals for presenting the coded image via multiple electrodes.

Aspects may include one or more of the following features.

An array of electrodes coupled to the output, for driving a different subset of electrodes using each different disjoint subset of the values.

An image acquisition device coupled to the input is selected from a group consisting of a video camera, a still-frame camera, a radar sensor, a sonar sensor, and an ultrasonic sensor.

In another aspect, in general, a visual prosthesis includes an input for accepting a signal representing an input image, a signal processor, and an array of electrodes. The signal processor is configured to sequentially select subsets of scan lines of pixels of an image, and for each selected subset of scan lines, form multiple blocks of pixels in the subset of scan lines, and for each of the blocks form transform coefficients from the block of pixels, and form signals for presentation of the transform coefficients of the blocks on corresponding electrodes, including forming signal pulses for sequential presentation of disjoint subsets of the values in successive time intervals. The array of electrodes is coupled to the signal processor for driving a different subset of electrodes using each different disjoint subset of the values.

In another aspect, an approach to coding for visual prostheses includes one or more of the following features:

1. Use of image compression techniques for coding strategies;
2. Use of a temporal coding of the image (ITCS);
3. Use of continuous interleaved sampling (CIS);
4. Use of radar/sonar (e.g., ultrasonic) information;
5. Use of the raw spectrogram instead of extracting the time-of-flight from an ultrasonic signal;
6. Use of a combination of visual and radar/sonar information.

Aspect may have one or more of the following advantages.

Previous research has indicated that standard image enhancement techniques, such as edge detection, are not useful in increasing the recognition of low-resolution images (25×25 pixels or below). Moreover, some research has shown that with 50×50 images, Sobel edge detection and Canny edge detection techniques perform worse than unprocessed images in picture recognition tasks. These results undermine the efficacy of standard image enhancement techniques in visual prosthesis apparatuses. One or more aspects described herein exploit a different approach that preliminary results indicate will successfully increase the recognition of low-resolution images (peculiar to state-of-the-art prosthesis). Implementations of the approaches described herein are not limited to retinal stimulation, but can be applied to all the possible sites of neural stimulation (e.g., brain cortex, optic nerve, and thalamus).

Other features and advantages of the invention are apparent from the following description, and from the claims.

and $\lambda = (8, 2, 1, 0.5)$.

DESCRIPTION

Figure 1:
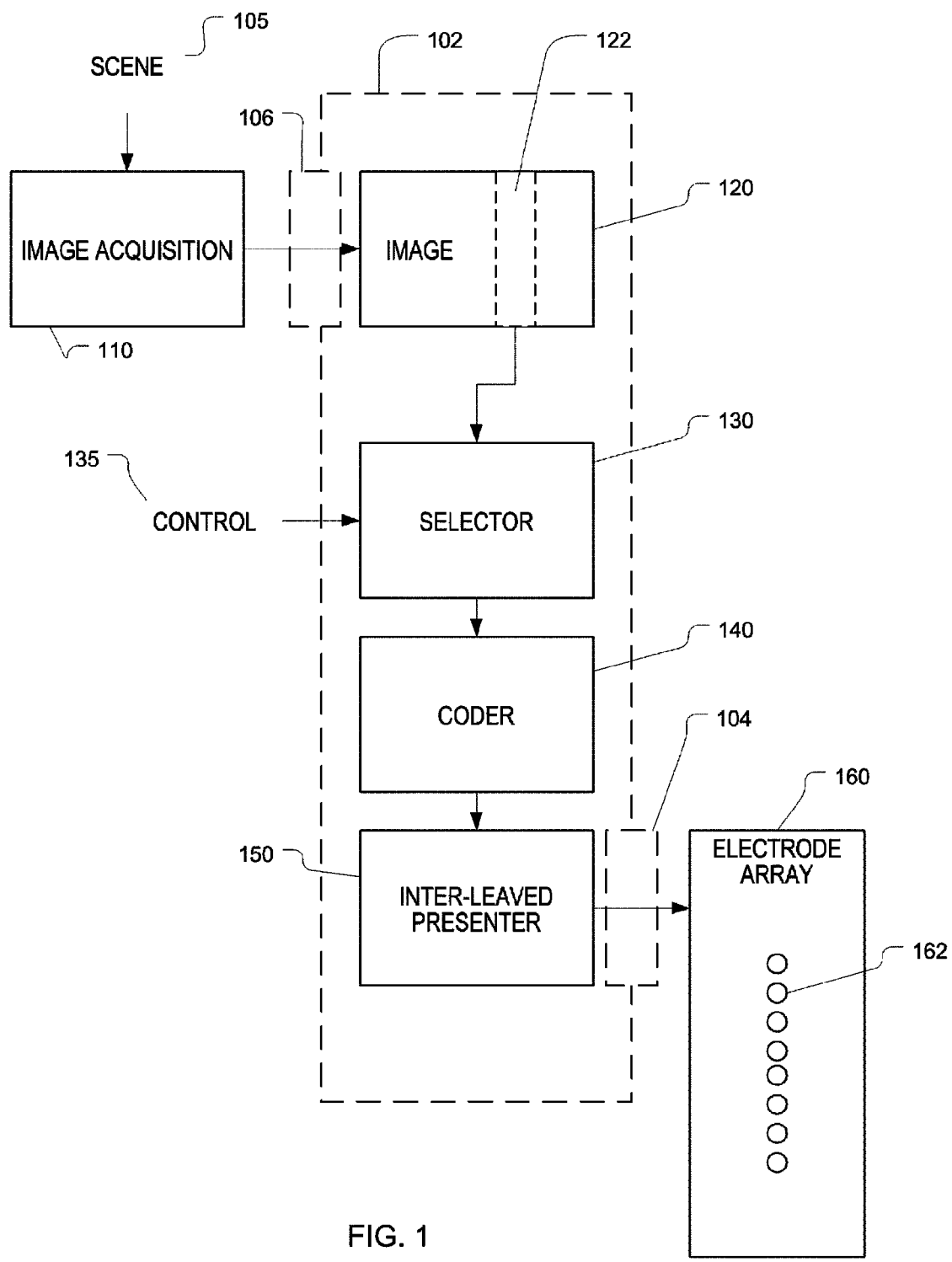
FIG. 1 is a block diagram of a prosthetic vision system.

Referring to FIG. 1, a prosthetic vision system 100 provides a way of presenting a visual scene 105 using an electrode array 160 that includes a number of individual electrodes 162 coupled to a subject's neural tissue. In general, the system includes an image acquisition module 110, which forms an image representation 120 from the scene 105. In some examples, the scene may be a physical scene that is acquired using a visible spectrum camera. In some examples, different types of acquisition modalities may be used to sense physical scenes, including non-visible light spectra, ultrasound, and radar. In some examples, the scene 105 is synthetic, for instance, representing text or other symbols (e.g., Braille) that are not necessarily printed, or representing a synthesized form of a physical scene, for example, a range map or a synthesis of multiple acquisition modalities. In some examples, a prosthetic device 102 includes an output 104 for driving the electrodes 160, and an input 106 for accepting the data from the image acquisition device 110. For instance, the output 104 transmits the signals for driving the electrodes as voltage or current encoded electrical signals, as optical signals, or as radio frequency signals. The prosthetic device may be coupled to the electrodes via electrical conductors, optical links (e.g., via optical fiber or free space optical communication), or may make use of a radio frequency link.

In some examples, the image 120 is explicitly represented as an array of pixel values stored in a memory, for instance an array of 80 by 80 pixels, each pixel represented as a intensity value (e.g., 0 . . . 255) as a binary number. Note that as part of the image acquisition process, an initial image may be acquired at a higher resolution and then downsampled using conventional image processing techniques. In some examples, the image is logically formed, but is not necessarily explicitly and/or concurrently represented as a whole image in a memory.

In some examples, successive portions 122 of the image 120 are selected by a selector 130. For instance, the portions form columns of multiple pixel lines (scan lines), for example, with each portion consisting of eight out of eighty pixel lines (i.e., the image can be divided into ten portions/columns). In some examples, the selector is controlled to cycle through the portions, for instance, cycling from left to right of the image, and then repeating the scan. As is discussed further below, in some examples, a control 135 is input to the selector 130 to determine the portion of the image to be processed. For instance, the control 135 may be determined from an estimate of a subject's direction of view of the scene.

The selected portion 122 of the image 120 is passed to a coder 140, which determines values for presentation to the subject via the electrode array 160. The values for presentation are then passed to an interleaved presenter 150, which controls the specific timing of the presentation of values on the electrodes 162 of the array, in some examples using a pulse signal representing the signal value, for instance, according to the amplitude of the pulse.

In an example described below, the coder 140 is based on a Discrete Cosine Transform approach. In this example, the image acquisition stage 110 downsamples a camera image to 80×80 pixels with conventional image processing techniques. The reader should recognize that this number of pixels and aspect ratio are only an example, and that other values may be used in other examples. The image is considered to be made up of blocks of 8×8 pixels. Successive columns of 8 blocks of pixels are selected for processing, passed to the coder 140, which, for each block, performs a discrete cosine transform (DCT) on the block. The DCT transforms pixels $i_{x,y}$ (rows and columns indexed for each block from 0 to 7) into a coefficients $I_{u,v}$, using the following formula:

$$I_{u,v} = \sum_{x=0}^{7}\sum_{y=0}^{7} i_{x,y}\cos\left[\frac{\pi}{8}\left(x+\frac{1}{2}\right)u\right]\cos\left[\frac{\pi}{8}\left(y+\frac{1}{2}\right)v\right].$$

Considering the image as a whole, the coder effectively determines a new matrix of 80×80 coefficients. In this example only the coefficients corresponding to the lowest six spatial frequency components, are used, rather than all 64 coefficients per block, and the other coefficients are neglected. That is, a total of 10×10×6=600 coefficients are passed from the coder 140 to the presenter 150 for each cycle through the image, which has 10×10 blocks of pixels.

Figure 2:
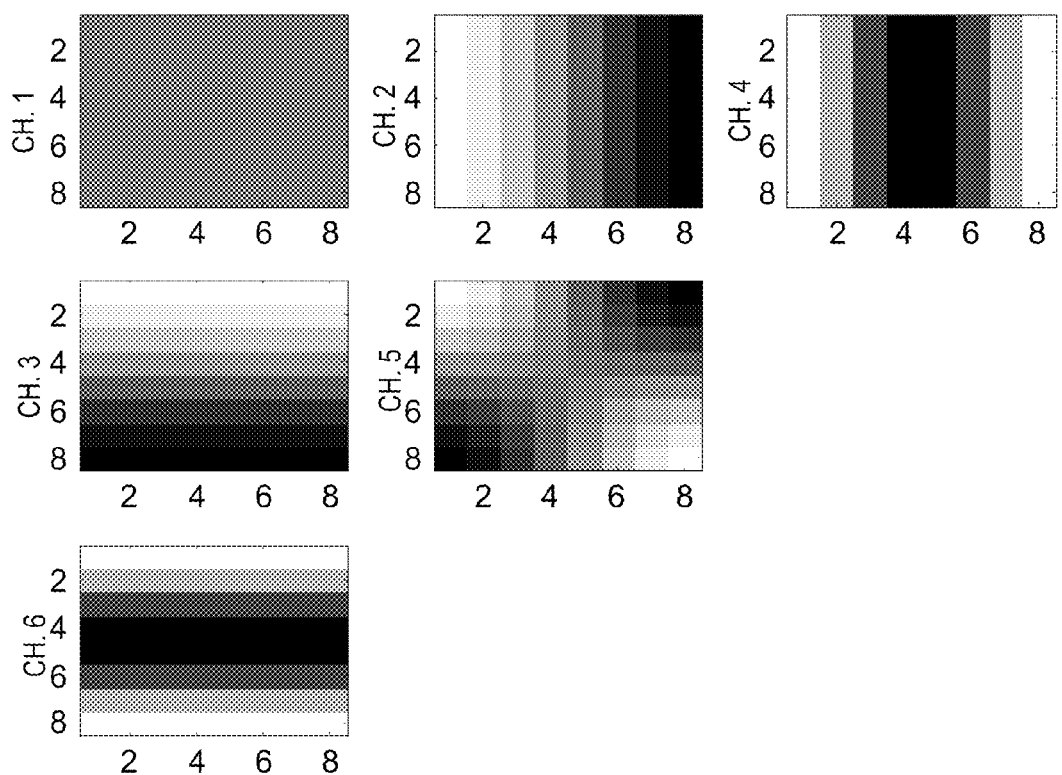
FIG. 2 is a depiction of kernel functions corresponding to low spatial frequency coefficients for a block using a discrete cosine transform (DCT).

Referring to FIG. 2, the computation of each of the six coefficients for each block corresponds to a summation of multiplication of pixel values with corresponding values of a kernel function, that is, as an inner product. The six kernel functions are represented in FIG. 2 in grayscale, labeled as channel 1 (CH. 1) through channel 6 (CH. 6) for that block (rows and columns are indexed 1 . . . 8 in the figure). The coder 140 quantizes the six coefficients for each block to a precision of 8 bits per coefficient.

Figure 3:
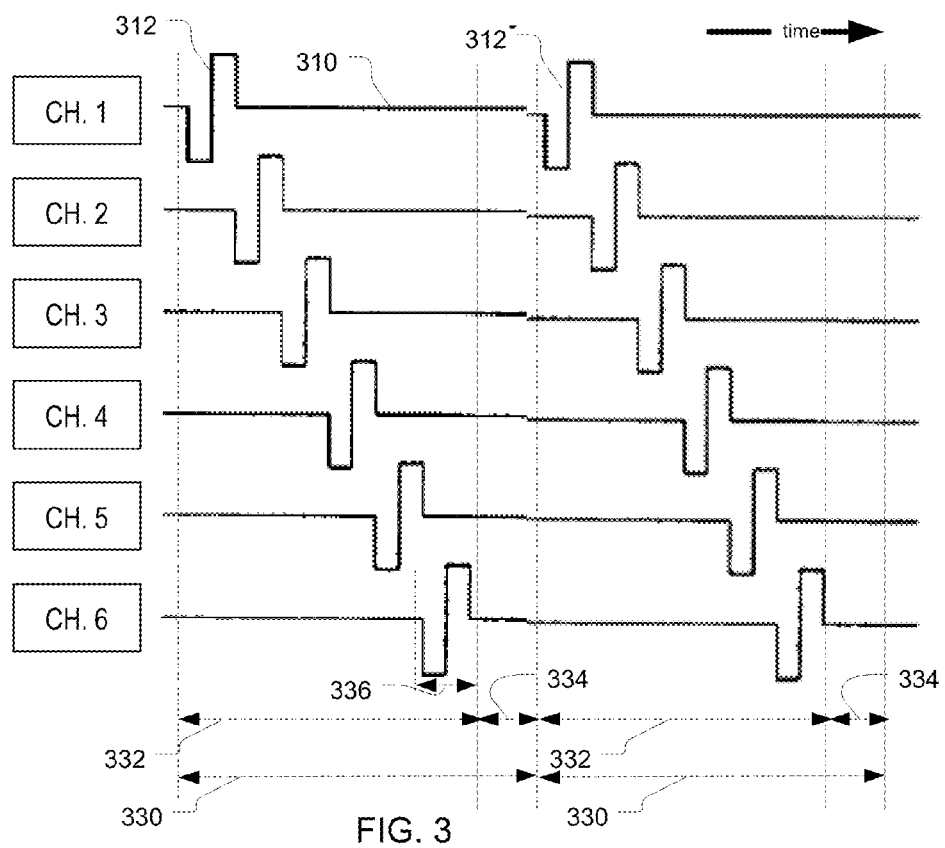
FIG. 3 are time signals for six channels corresponding to one block of an image.

The interleaved presenter 150 receives the quantized coefficients and temporally codes the coefficients for presentation via the electrode array 160. In the present example, the electrode array has 60 electrodes 162, 10 groups of 6 electrodes allowing presentation of all the blocks in the selected portion of the image using a separate electrode for each coefficient value. Within each group of six electrodes, the six coefficients for the corresponding image block are temporally coded with a continuous interleaved sampling (CIS) strategy using six corresponding electrode channels. Referring to FIG. 3, six channels (labeled CH. 1 through CH. 6) of electrode signals 310, each correspond to one of six coefficients for one block of the image, are coded in a continuous interleaved sampling (CIS) approach. In this example, a channel stimulation rate of 100 pulses per second is used. That is, the pulse rate on any particular channel is 100 pulses per second, or equivalently, a period of 10 ms (block duration 330 shown in the FIG. 3). For a particular channel, cycling through the 10 blocks (one block per column) takes 100 ms. Before cycling through the columns of the image again, a 20 ms pause is inserted (not illustrated), for a total image frame period of 120 ms, which permits a frame rate of approximately 8 Hz. During each period 330, the signaling pulses 312 on each signal line 310 are offset in time. For instance, each pulse width 336 is offset such that the pulses on different of the six channels per block do not overlap in time, with each channel being successively offset. Optionally, a final period 334 between columns is inactive on all electrodes. Each of the 10 blocks of six electrodes (i.e., a total of 60 electrodes) follows this same scheme (two blocks being illustrated in FIG. 3), such that in each group of six electrodes, only one electrode has a signaling pulse at a time. In some examples, the geometric arrangement is such that electrodes for the same channel number for different blocks that are concurrently presented (e.g., in the same column) are maximally separated, thereby avoiding spatial channel interactions (e.g., interfering physical and/or perceptual phenomena) in that group. For example, in a linear arrangement of the 60 electrodes, electrodes 1, 7, 13, . . . , 55 may all be assigned to CH. 1, electrodes 2, 8, 14, . . . , 56 may be assigned to CH. 2, etc. Note that in other embodiments, a different assignment of electrodes may be used. For instance, the linear order of the channels may be different (e.g., CH. 1, 5, 2, 4, 6, 3 rather than CH. 1, 2, 3, 4, 5, 6 as illustrated). In other embodiments, a non-linear arrangement of electrodes may be used, for instance, a rectangular array, while still providing spatial separation between electrodes of a same channel group (e.g., CH. 1).

Figure 4A:
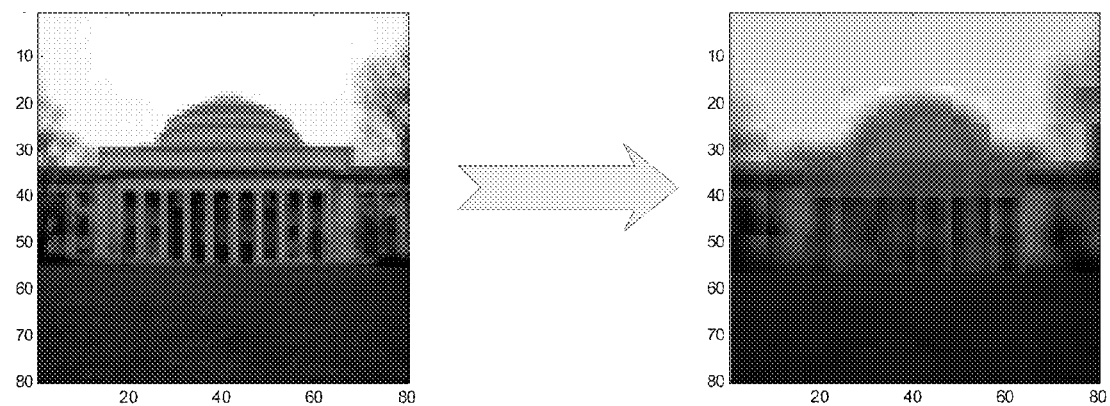
FIGS. 4A-C are images that depict information retained using six coefficients per block for a landscape image, a face image, and a text image.
Figure 4B:
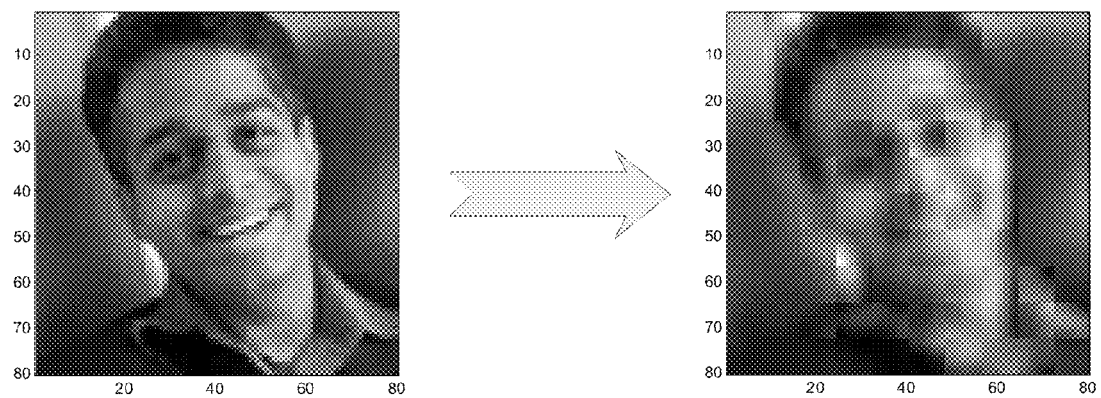
Figure 4C:
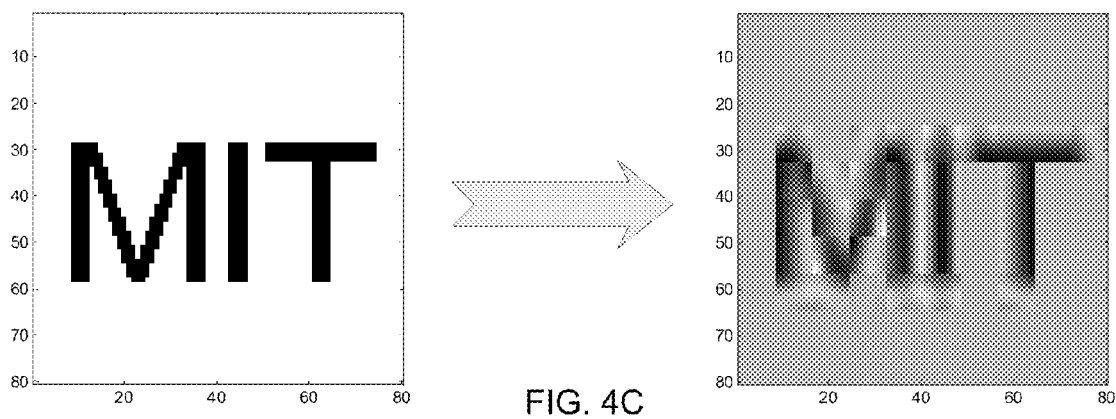

The effectiveness of the coding strategy using 8-bit quantization retaining only the 6 coefficients of each block is illustrated in FIGS. 4A-C where the original and the pictures from the quantized coefficients are shown. Landscape, face, and text pictures are all well represented in the reconstructed images.

In some embodiments, a set of channels effectively present a constant "bar" during the presentation of an image (e.g., during the 100 ms of the 120 ms frame period). For instance, the bottom row of blocks (i.e., the bottom 8 pixel rows) may be presented with constant pulse level on one or more of the six channels, in order to provide the subject with an indication of the presence of an image. It is expected that a subject will have the sensation of a sliding column window that illuminates the image of interest. The fast process (e.g., eight pictures every second) is chosen so that a complete picture is mentally reconstructed. In embodiments in which a sliding grey bar is "visible" at the bottom of the image, the bar provides a reminder of where the complete image is.

In alternative embodiments, the picture is coded row-by-row rather than column-by-column as described in the example above. In other embodiments, different subset of pixels may be selected each time period. For instance, a row, column, rectangular or circular region, etc., may be selected in some repeating pattern, or based on the provided control signal.

In another embodiment, the coder does not necessarily perform a transform of the image pixel values. For instance, the selector 130 selects a subset of pixels 122 from the original image, and the coder 140 performs little or no processing of the pixel values in the selected portion before passing the values to the presenter 150. In this embodiment, the image is coded temporally (ITCS): the entire image is not simultaneously coded, but at each time only a portion of the image is coded. For that portion that is presented, each electrode is used to present one of the pixel values, and the set of electrodes are driven using a temporal coding that offsets the signaling pulses on different channels to mitigate spatial interference effects.

In some embodiments, the set of pixels that is selected follows a random or pre-determinate movement (e.g., cycloidal movement) within the image. A particular example of this embodiment is a strategy that codes a picture of 80×80 pixels by selecting a different box of 10×10 pixels every 10 ms; the 10×10 pixels are located by moving this box every 10 ms in a random direction (not allowing the box to exit the image of interest). The sequence of these 100 pixels every 10 ms constitutes the temporal coding of the image, and the corresponding information is sent to 100 electrodes. This process could also be controlled by an external signal, such as the information obtained by tracking the subject's eye movements.

In another embodiment, the entire image is coded, for instance generating a 10×10 array of values for each of six coefficients of a DCT (i.e., 10×10×6=600 coefficients). A selector then selects portions of the coded image not column-by-column, but kernel-by-kernel, i.e., each time, only the coefficients corresponding to a specific kernel are simultaneously sent to the electrodes. For instance, an array of 10×10=100 electrodes are used. The information related to each of these six pictures is sent to the electrodes in six successive presentation periods to cycle through the coefficients for one image frame.

In another embodiment, a block-based transform approach is not necessarily used. In this approach a set of kernels consisting of a two-dimensional Gabor kernel with various scales, rotations, and positions is created. The kernels are matched with the image of interest, which is then decomposed into a set of coefficients, similar to what has been shown in the previous embodiment using the DCT. The Gabor kernel is defined by $$g(x, y, x_0, y_0, \lambda, \theta, \psi, \sigma, \gamma) = e^{-\left(\frac{x'^2+\gamma^2 y'^2}{2\sigma^2}\right)} \cos\left(2\pi \frac{x'}{\lambda} + \psi\right)$$

where $$x'=(x-x_0)\cos\theta+(y-y_0)\sin\theta$$

$$y'=-(x-x_0)\sin\theta+(y-y_0)\cos\theta$$

Figure 5:
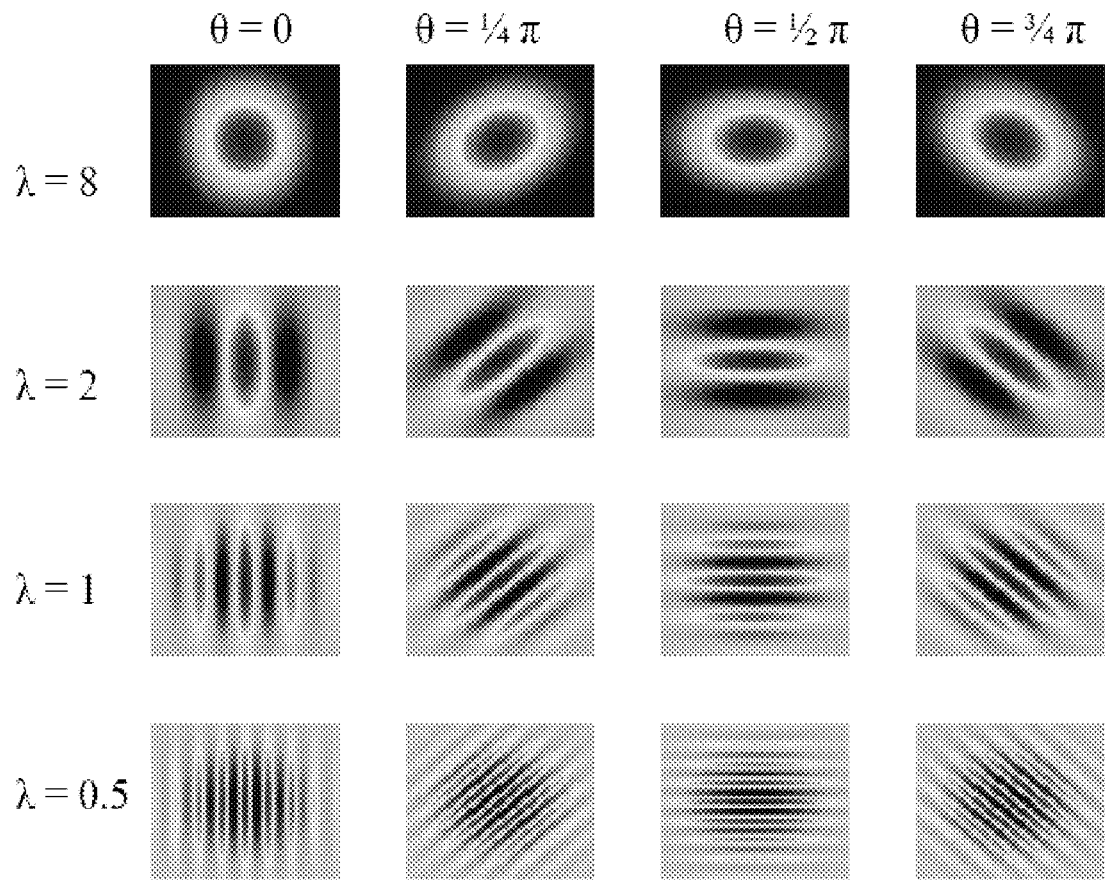
FIG. 5 is a depiction of a set of Gabor kernels with $$x_0 = 0, y_0 = 0, \psi = 0, \sigma = 1, \gamma = 2, \theta = \left(0, \frac{1}{4}\pi, \frac{1}{2}\pi, \frac{3}{4}\pi\right),$$

In this equation, $\lambda$ represents the wavelength, $\theta$ represents the orientation, $\psi$ is the phase offset, and $\gamma$ is the spatial aspect ratio. The center of the kernel is set by $x_0$ and $y_0$. FIG. 5 shows an example of a set of kernels with $x_0=0$, $y_0=0$, $\psi=0$, $\sigma=1$, $\gamma=2$, $$\theta = \left(0, \frac{1}{4}\pi, \frac{1}{2}\pi, \frac{3}{4}\pi\right),$$

and $\lambda=(8, 2, 1, 0.5)$. That is, a total of 16 kernels are defined in this way.

In this embodiment, each kernel is used to compute one coefficient, and the set of computed coefficients are passed to the presenter 150, which forms the CIS signals for driving the electrode array, for example, with 16 electrodes, one for each kernel shown in FIG. 5. In some examples, the 16 electrodes are driven such that each channel has a different time offset for its signal pulse. In some examples, the electrodes are grouped (e.g., into 4 groups) and the channels/electrodes in a group use concurrent signaling pulses.

In some examples, the parameters of the kernel function (e.g., the location and/or orientation parameters) are selected according to a control signal (e.g., based on direction of view), or selected according to a signal processing of the image to determine a region of likely interest, or are varied according to a cyclical or random pattern.

It should be understood that the approaches described above are not limited to presentation of images acquired with visible light. In some embodiments, information extracted by a radar/sonar apparatus is presented in this way, for instance, by forming a synthetic image. Radar and/or sonar information can be extremely beneficial to a person with limited vision for efficiently navigating in complex environments. A radar/sonar signal, e.g., the signal coming from an ultrasound transducer, can be filtered in some frequency bands, and the information related to the envelopes of these signals fed to the prosthesis. Note that for some signal acquisition modalities, a transmitter may be integrated into the prosthesis, for example, to emit a radar, sonar, or ultrasound signal, that is then acquired after interaction (e.g., reflection) with the environment of the subject.

As introduced above, in some embodiments, it is possibility to control the characteristic parameters of the signal acquisition and/or selection (e.g., radar/sonar-pointing direction) by eye movement. In this case, an apparatus able to detect eye movement is used in combination with our invention. In particular, a beam-forming strategy (driven by eye position) can be used in conjunction with a multitude of ultrasound sensors.

In another embodiment, the visual prostheses is used to present text or other symbols. One approach to presenting such symbols is to form successive images that contain the letters, for example, as black-and-white images. These synthesized images are then processed in the same manner as other types of acquired images. Another approach to presenting text can also be used, in which the characters are mapped to tuples of dots, such as in the Braille system where every character is represented with a tuple of six dots. The corresponding information is then fed to the electrodes, for instance coding the presence or absence of a Braille dot for each letter. The sequence of characters can be controlled by the subject, e.g., using a keyboard, using a joystick, or moving the eyes.

Embodiments of the approaches described above may be implemented in hardware, in software, or using a combination of hardware and software. Hardware implementations may include special purpose integrated circuits, for example, application specific integrated circuits (ASIC). Software can include instructions for causing a data processor to perform functions described above. For instance, the processor can include a digital signal processor. In some implementations, the functional blocks are integrated into a single device. In other implementations, various components are implemented separately. For example, the image acquisition element may be separate and communicates using a wired or wireless technique with the coder and/or presenter modules.

It is to be understood that the foregoing description is intended to illustrate and not to limit the scope of the invention, which is defined by the scope of the appended claims. Other embodiments are within the scope of the following claims.

What is claimed is:

1. A method for coding information for prosthetic visual presentation, the method comprising:
   sequentially selecting portions of an image; and
   for each selected portion,
      forming a plurality of values to represent the portion, and
      forming signals for presentation of the plurality of values representing the portion of the image on corresponding electrodes, including forming signals for sequential presentation of a plurality of disjoint subsets of the values in corresponding successive time intervals;
   wherein the image is represented as a plurality of scan lines of pixels, and each selected portion includes a corresponding subset of the scan lines of the image; and
   wherein forming the plurality of values to represent the selected portion of the image includes forming a plurality of blocks of pixels in the subset of scan lines, and forming a transform representation of each of the blocks of pixels.

2. The method of claim 1 further comprising repeating the sequential selection of portions of the image, and forming the values and forming the signals for the selected portions, are repeated for successive images.

3. The method of claim 1 wherein forming the plurality of values to represent the selected portion of the image includes forming a plurality of subunits of the portion, and forming a subset of the values to represent each subunit.

4. The method of claim 3 wherein each of the disjoint subsets of values includes values used to represent multiple of the subunits of the selected portion.

5. The method of claim 1 wherein forming the transform representation includes forming values as Discrete Cosine Transform (DCT) coefficients of the block of pixels.

6. The method of claim 5 wherein forming the values as DCT coefficients includes disregarding at least some DCT coefficients of the block of pixels.

7. The method of claim 1 wherein each disjoint subset of values includes corresponding values of a DCT coefficient of multiple of the blocks of pixels.

8. The method of claim 1 wherein sequentially selecting the portions of the image comprises sequentially selecting the portions in a predetermined cycle.

9. The method of claim 1 wherein sequentially selecting the portions of the image comprises selecting portions of the image according to a control signal.

10. The method of claim 9 wherein the control signal represents at least one of a joystick signal and an eye tracking signal.

11. The method of claim 1 wherein forming the values representing the selected portion of the image comprises forming quantized values.

12. The method of claim 1 further comprising presenting the formed signals to a subject to elicit a perception of the image.

13. The method of claim 1 further comprising driving electrodes using the formed signals.

14. The method of claim 13 wherein for each selected portion of the image, driving the electrodes comprises driving a different subset of electrodes using each different disjoint subset of the values.

15. The method of claim 13 wherein driving the electrodes includes transmitting the formed signal to a region of one or more of a retina, an optic nerve, a thalamus, and a cortex of a brain.

16. The method of claim 1 further comprising acquiring the image from an imager that includes one or more of a video camera, a still-frame camera, a radar sensor, a sonar sensor, and an ultrasonic sensor.

17. The method of claim 16 further comprising controlling the imager using an external signal.

18. The method of claim 17 wherein the external signal is provided by one or more of an eye-tracking system, physiological measurements, a joystick, or a keyboard.

19. The method of claim 1 wherein the image comprises an image of one or more of a landscape, a face, or text.

20. The method of claim 1, further comprising adding a graphical element to the image that is indicative of a part of the image that is currently selected.

21. The method of claim 1 wherein the image includes a graphical representation of text, each portion of the image including at least one character of the text.

22. The method of claim 21 wherein the graphical representation of the text includes at least one of a graphical representation of a character glyph, a Braille code, a Morse code, and a user-defined code.

23. A method for coding information for prosthetic visual presentation the method comprising:
sequentially selecting portions of an image; and
for each selected portion,
forming a plurality of values to represent the portion, and
forming signals for presentation of the plurality of values representing the portion of the image on corresponding electrodes, including forming signals for sequential presentation of a plurality of disjoint subsets of the values in corresponding successive time intervals;
wherein sequentially selecting portions of the image comprises selecting processing of the image according to selected kernel functions.

24. The method of claim 23 wherein the image is represented as a plurality of scan lines of pixels, and each selected portion includes a corresponding subset of the scan lines of the image.

25. The method of claim 24 wherein forming the plurality of values to represent the selected portion of the image includes forming a plurality of blocks of pixels in the subset of scan lines, and forming a transform representation of each of the blocks of pixels.

26. The method of claim 23 wherein the kernel functions comprise a set of Gabor kernel functions, each characterized by at least some of scale, rotation, and scale parameters.

27. A visual prosthesis comprising:
an input for accepting a signal representing an input image;
a signal processor configured to sequentially select portions of the image, and for each selected portion, form a plurality of values to represent the portion, and form signals for presentation of the plurality of values representing the portion of the image on corresponding electrodes, including forming signals for sequential presentation of a plurality of disjoint subsets of the values in successive time intervals;
an array of brain electrodes; and
an output for providing the formed signals for presenting the coded image via the array of electrodes by driving a different subset of electrodes using each different disjoint subset of the values, the subsets of electrodes being interleaved in the array such that each subset of electrodes is selected to exclude adjacent electrodes in the array thereby avoiding physical and/or perceptual interactions between presented values of each disjoint subset of the values.

28. A visual prosthesis comprising:
an input for accepting a signal representing an input image;
a signal processor configured to
sequentially select subsets of scan lines of pixels of an image, and
for each selected subset of scan lines, form a plurality of blocks of pixels in the subset of scan lines, and for each of the blocks form a plurality of transform coefficients from the block of pixels, and form signals for presentation of the transform coefficients of the blocks on corresponding electrodes, including forming signal pulses for sequential presentation of a plurality of disjoint subsets of the values in successive time intervals; and
an array of electrodes coupled to the signal processor, for driving a different subset of electrodes using each different disjoint subset of the values.

29. The visual prosthesis of claim 28 wherein the input comprises:
an image acquisition device coupled to the input selected from a group consisting of a video camera, a still-frame camera, a radar sensor, a sonar sensor, and an ultrasonic sensor.

* * * * *